US005443485A

United States Patent [19]
Housworth et al.

[11] Patent Number: 5,443,485
[45] Date of Patent: Aug. 22, 1995

[54] APPARATUS AND METHOD FOR CAPTURE DETECTION IN A CARDIAC STIMULATOR

[75] Inventors: Craig M. Housworth; Edward A. Schroeppel, both of Lake Jackson, Tex.

[73] Assignee: Intermedics, Inc., Angleton, Tex.

[21] Appl. No.: 117,854

[22] Filed: Sep. 8, 1993

[51] Int. Cl.[6] ............................................. A61N 1/37
[52] U.S. Cl. ............................................. 607/28
[58] Field of Search ............................ 607/11, 13, 28

[56] References Cited

U.S. PATENT DOCUMENTS

| 4,114,627 | 9/1976 | Lewyn . | |
|---|---|---|---|
| 4,373,531 | 2/1983 | Wittkampf . | |
| 4,537,201 | 8/1985 | Delle-Vedove | 128/697 |
| 4,543,956 | 10/1985 | Herscovici | 128/419 |
| 4,649,931 | 3/1987 | Beck . | |
| 4,674,508 | 6/1987 | DeCote . | |
| 4,674,509 | 6/1987 | DeCote, Jr. | 607/28 |
| 4,686,988 | 8/1987 | Sholder . | |
| 4,759,366 | 7/1988 | Callaghan . | |
| 4,759,367 | 7/1988 | Callaghan . | |
| 4,766,900 | 8/1988 | Callaghan . | |
| 4,766,901 | 8/1988 | Callaghan . | |
| 4,827,934 | 5/1989 | Ekwall . | |
| 4,858,610 | 8/1989 | Callaghan et al. | 607/28 |
| 4,878,497 | 11/1989 | Callaghan . | |
| 4,895,152 | 1/1990 | Callaghan . | |
| 4,979,507 | 12/1990 | Heinz et al. . | |
| 4,996,986 | 3/1991 | Thomassen . | |
| 5,018,523 | 5/1991 | Bach, Jr. et al. . | |
| 5,033,473 | 7/1991 | Wang et al. | 128/696 |
| 5,127,401 | 7/1992 | Grevious . | |
| 5,184,615 | 2/1993 | Nappholz et al. . | |
| 5,265,601 | 11/1993 | Mehra | 607/9 |
| 5,265,603 | 11/1993 | Hurdrlik | 607/61 |

Primary Examiner—William E. Kamm
Assistant Examiner—Scott M. Getzow
Attorney, Agent, or Firm—Richard L. Robinson

[57] ABSTRACT

A capture detection circuit for an implantable cardiac stimulator. A signal detected by an electrode in the heart following delivery of a stimulating pulse is amplified, bandpass and highpass filtered, rectified, integrated over a selected window of time starting at a selected delay after delivery of the stimulating pulse, and applied to two comparators having different reference values. If the integrated signal exceeds the first reference value, the first comparator output goes high. If the integrated signal exceeds the second reference value, the second comparator goes high. If both comparators remain low, non-capture is indicated. If the first comparator goes high and the second comparator remains low, capture is indicated. If the second comparator goes high, an intrinsic contraction is indicated. The window of integration can be extended to distinguish capture from intrinsic contraction.

15 Claims, 3 Drawing Sheets

NON-CAPTURE

CAPTURE

INTRINSIC

APPARATUS AND METHOD FOR CAPTURE DETECTION IN A CARDIAC STIMULATOR

BACKGROUND OF THE INVENTION

1. Field of the Invention

The present invention relates generally to cardiac pacing using an implantable cardiac stimulator, and more particularly to verification of capture of the heart following application of an electrical stimulating pulse by the cardiac stimulator.

2. Background Information

A cardiac stimulator, or pacemaker, "captures" the heart by delivering an electrical pulse to the myocardium of a selected chamber during an interval in the cardiac cycle in which the cardiac tissue is excitable. The electrical pulse causes depolarization of cardiac cells and a consequent contraction of the chamber, provided that the energy of the pacing pulse as delivered to the myocardium exceeds a threshold value.

It is desirable to adjust the pacemaker so that the energy delivered by the electrical pulse to the myocardium is at the lowest level that will reliably capture the heart. Such a level assures therapeutic efficacy while maximizing the life of the pacemaker battery. Because the threshold for capture varies from one implantation to another, and can change over time, it is also desirable that the pulse energy delivered by the pacemaker to the myocardium be adjustable during and subsequent to implantation. Adjustment can be effected manually from time to time through use of an external programmer that communicates with the implanted pacemaker. It would be more desirable, however, to provide a pacemaker that adjusts the pulse energy itself automatically and dynamically in response to changes in the capture threshold.

Changes in capture threshold can be detected by monitoring the efficacy of stimulating pulses at a given energy level. If capture does not occur at a particular stimulation energy level which previously was adequate to effect capture, then it can be surmised that the capture threshold has increased and that the stimulation energy level should be increased. On the other hand, if capture occurs consistently at a particular stimulation level over a relatively large number of successive stimulation cycles, it is possible that the stimulation threshold has decreased and that pacing energy is being delivered at an energy level higher than necessary. This can be verified by lowering the stimulation energy level and monitoring for loss of capture at the new energy level.

For automatic and dynamic adjustment of the stimulation energy level to be successful, it is necessary for the implantable cardiac stimulator to be able to verify that capture has occurred. Capture verification is generally accomplished by detecting an electrical potential in the heart evoked by the stimulating pulse. If capture has not occurred, there will be no evoked potential to detect. It follows that each time a stimulating pulse is delivered to the heart, the heart can be monitored during an appropriate period of time thereafter to detect the presence of the evoked potential, and thereby verify capture. In practice, however, reliable detection of the evoked potential is not a simple matter, especially where it is desired to sense the evoked potential with the same electrode that delivers the stimulating pulse. This is because the evoked potential is small in amplitude relative to the residual polarization charge on the electrode resulting from the stimulation pulse. The residual charge decays exponentially but tends to dominate the evoked potential for several hundreds of milliseconds thereafter. Several techniques for alleviating the effects of the residual charge are disclosed in the prior art.

U.S. Pat. No. 4,858,610, issued Aug. 22, 1989, to Callaghan et al., teaches the use of charge dumping following delivery of the stimulating pulse to decrease lead polarization and also the use of separate pacing and sensing electrodes to eliminate the polarization problem on the sensing electrode. U.S. Pat. No. 4,686,988, issued Aug. 18, 1987, to Sholder, teaches the use of a separate sensing electrode connected to a detector for detecting P-waves in the presence of atrial stimulation pulses, wherein the P-wave detector has an input bandpass characteristic selected to pass frequencies that are associated with P-waves. U.S. Pat. No. 4,373,531 teaches the use of pre-and post-stimulation recharge pulses to neutralize the polarization on the lead. U.S. Pat. No. 4,537,201 teaches a linearization of the exponentially decaying sensed signal by applying the sensed signal through an anti-logarithmic amplifier in order to detect a remaining nonlinear component caused by the evoked potential. U.S. Pat. No. 4,674,509, issued Jun. 23, 1987, to DeCote, Jr. teaches the generation of paired pacing pulses spaced such that at most only one pulse of each pair can induce capture. The waveforms sensed through the pacing lead following the generation of each of the pair of pulses are electronically subtracted to yield a difference signal indicative of the evoked cardiac response.

Each of the prior art approaches to detecting a small-amplitude evoked potential in the presence of a large amplitude residual charge from a stimulating pulse has significant disadvantages. Those techniques that depend upon the use of a separate electrode located at some distance from the stimulating electrode so as to be isolated from the residual stimulating charge attempt to avoid the detection problem at the cost of requiring a separate sensing electrode. Those approaches that depend upon delivering an opposite-polarity charge to the electrode to neutralize the residual charge, and those approaches that depend upon delivering a pair of close-spaced pacing pulses are unnecessarily wasteful of battery power as well as being unduly complex. The approach that depends upon use of an anti-logarithmic amplifier to compensate for the generally exponential decay of the residual charge requires unnecessarily complex circuitry that is difficult to implement.

It would be desirable to provide a relatively simple and easily implemented capture verification circuit for use in an implantable cardiac stimulator that would permit detection of cardiac evoked potentials in the presence of a residual charge from a preceding stimulation pulse, and that permits use of the same electrode to sense the evoked response as was used to deliver the stimulation pulse. This and other desirable goals are met by the present invention.

SUMMARY OF THE INVENTION

Data collected in humans from implanted endocardial pacing leads has revealed a detectable difference between the capture and non-capture morphologies of the signal detected by the pacing lead. Although a lead polarization voltage that decays exponentially back to zero after the pacing pulse is present during both capture and non-capture, a small higher-frequency signal inflection superimposed on the lead polarization curve is noted when capture has occurred. It is believed that this inflection is generated by the depolarization of large cardiac muscle masses, such as the septum or free walls of the heart.

In accordance with one aspect of a preferred embodiment of the present invention, an apparatus and method is taught for processing the signal detected from an implanted lead to detect the presence of the small capture inflection. The signal is first bandpass filtered to eliminate high-frequency noise and to remove much of the effect of the lead polarization voltage. The signal is then highpass filtered to remove any remaining polarization voltage and to accentuate the evoked response signal, which contains higher frequency components than the residual polarization decay waveform. The resultant signal is integrated over a short time window starting at a selected delay following delivery of the pacing pulse. The output of the integrator is passed to a comparator having a reference voltage. If the value of the integral goes above the reference voltage within the integration window, the comparator goes to a logic high level, indicating that capture has occurred. If, by the end of the integration window, the integrator output has not exceeded the reference voltage, the comparator output remains low, indicating that the stimulating pulse has failed to capture the heart.

Intrinsic contractions that occur near the time of delivery of a non-capturing stimulating pulse may generate relatively large signals that fall within the integration window. Such intrinsic contractions result in the integrator stage having very large output values that could cause the voltage reference to be exceeded in the comparator stage, leading to a false detection of capture.

In accordance with another aspect of a preferred embodiment of the present invention, two comparators are provided with different reference voltages. One comparator is set with a high reference level that will only be exceeded in the case of an intrinsic contraction. The other comparator is set with a lower reference level selected to detect capture signals. If both comparators indicate that their respective reference levels have been exceeded by the end of the integration window, an intrinsic contraction has occurred. If only the comparator with the lower reference level indicates that its reference level has been exceeded, a capture has occurred. If both comparators indicate that their respective reference levels have not been exceeded, the stimulating pulse did not capture the heart.

It is an object of the present invention to provide an improved, yet simple apparatus and method for detecting capture of the heart by a stimulating pulse delivered by an implantable cardiac stimulator.

It is a further object of the invention to provide an apparatus and method for detecting capture of the heart that can distinguish intrinsic contractions from contractions evoked in response to delivery of a stimulating pulse by an implantable cardiac stimulator.

Other objects and advantages of the present invention will be apparent from the following descriptions of a preferred embodiment with reference to the drawings.

DETAILED DESCRIPTION OF THE PREFERRED EMBODIMENT

Figure 1:
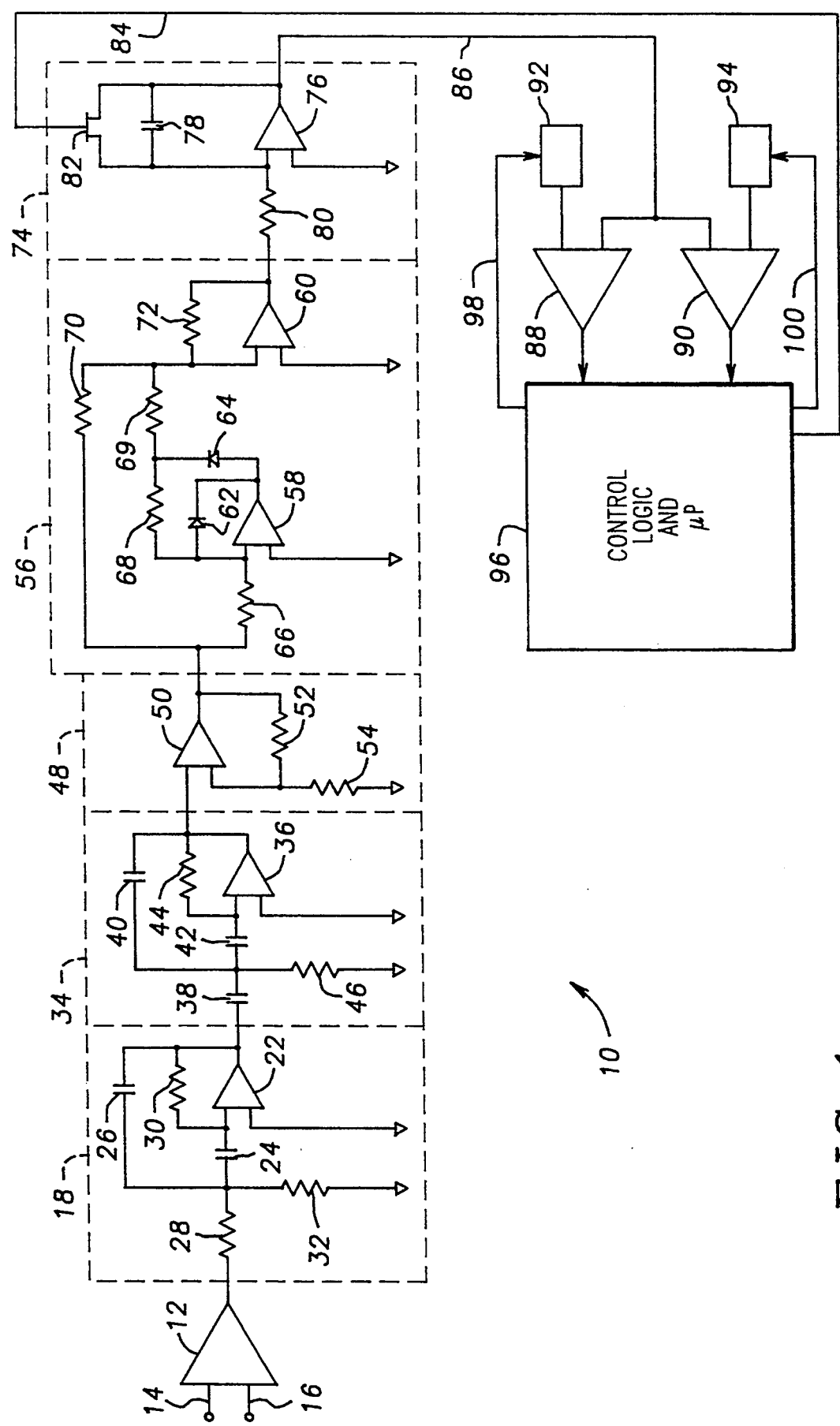
FIG. 1 is a block diagram of a circuit that is useful in an implantable cardiac stimulator for detecting capture of the heart following provision of a stimulating pulse by the cardiac stimulator. Some blocks of the diagram are illustrated further with representative schematic diagrams of the circuitry designated by such blocks.

Referring in particular to FIG. 1, there is illustrated a block diagram of a capture detection circuit 10 for use in an implantable cardiac stimulator. For clarity, circuit 10 as illustrated involves only that portion of the complete circuitry of an implantable cardiac stimulator with which the present invention is concerned. It will be understood by those skilled in the art that additional well-known circuitry for generating stimulating pulses, for example, will also be required in a complete device.

The present invention contemplates detecting capture of the heart by sensing via an electrode placed in the heart an electrical potential evoked in response to application of a stimulating pulse. A significant advantage of the present invention is that the same electrode that is used to deliver the stimulating pulse can also be used for detecting capture. This allows use of unipolar pacing between the lead tip and the pacer can without requiring a separate ring electrode for capture detection. Alternatively, bipolar pacing between the lead tip and ring electrode can be used without requiring a third electrode. In addition, when using bipolar pacing the tip electrode can be used as the capture detection electrode.

Again referring to FIG. 1, pre-amplifier 12 has a pair of inputs 14 and 16 between which sensed electrical activity signals from the heart are applied. In the preferred embodiment as described herein, input 14 is electrically connected via a first conductor of an endocardial lead to a tip electrode located in the ventricle of the heart, and input 16 is electrically connected to an external conductive surface of the pacemaker housing or "can." Nevertheless, it should be understood that input 14 can also be connected to a ring electrode, with input 16 connected to the can, or input 14 can be connected to the tip electrode with input 16 connected to the ring electrode. Input 14 can also be connected to an electrode located in an atrium of the heart.

The amplified output signal of pre-amplifier 12 is applied to the input of a following bandpass filter stage 18. Filter stage 18 is a second-order active bandpass filter implemented by an operational amplifier 22. The bandpass characteristics and gain of bandpass filter 18 are determined by capacitors 24 and 26, and by resistors 28, 30 and 32 arranged as shown in well-known fashion. Bandpass filter 18 has a voltage gain of 1.0, a center frequency of 37 Hz, and a Q of 0.825. The pass band is about 22 Hz to about 60 Hz.

The filtered output signal from bandpass filter 18 is applied to the input of a following highpass filter stage 34. Filter stage 34 is a second-order active highpass filter implemented by an operational amplifier 36. The highpass characteristics and gain of highpass filter 34 are determined by capacitors 38, 40 and 42 and resistors 44 and 46 arranged as shown in well-known fashion. Highpass filter 34 has a voltage gain of 1.32, a center frequency of 40 Hz and a Q of 0.707. The pass band is above about 40 Hz.

It should be appreciated that bandpass filter stage 18 and the immediately following highpass filter stage 34, when considered together, are in effect a single bandpass filter with more poles of filtering on the low frequency side of the pass band, resulting in a steeper signal rolloff on the low frequency side. The pass band resulting from filter stages 18 and 34 is about 40 Hz to about 60 Hz.

The filtered output signal from highpass filter 34 is applied to the input of a following amplifier stage 48. Amplifier 48 is implemented by an operational amplifier 50. The gain of amplifier stage 48, which is about 100, is determined by resistors 52 and 54 arranged as shown in well-known fashion.

The amplified output signal of amplifier stage 48 is applied to the input of a following precision full-wave rectifier or absolute value stage 56. Absolute value stage 56 is implemented by operational amplifiers 58 and 60, diodes 62 and 64, and resistors 66, 68, 69, 70 and 72 arranged as shown in well-known fashion.

The rectified output signal of absolute value circuit 56 is applied to the input of a following integrator stage 74. Integrator 74 is implemented by an operational amplifier 76. The integrating characteristics of integrator stage 74 are determined by capacitor 78 and resistor 80 arranged as shown in well-known fashion. An FET transistor switch 82 is connected in parallel with integrating capacitor 78 such that the drain terminal of FET 82 is connected to one terminal of capacitor 78 and the source terminal of FET 82 is connected to the other terminal of capacitor 78. Integrator 74 can be "cleared" by applying an appropriate signal to the gate terminal of FET 82 via line 84 to switch FET 82 on, thereby providing a conduction path between the source and drain terminals through which capacitor 78 is discharged.

The integrated output signal of integrator stage 74 is applied via line 86 to one input of each of two comparators 88 and 90. Each of the other inputs of comparators 88 and 90 are connected to variable reference voltage sources 92 and 94, respectively. The reference voltage source 92 of the first comparator 88 is set at a voltage level lower than that of the reference voltage source 94 of the second comparator 90. The output signal of each of comparators 88 and 90 is applied to a separate input of control logic and microprocessor circuit 96. Logic circuit 96 also has an output connected to line 84 for providing a signal to control the resetting, or clearing, of integrator stage 74 as described above. In addition, logic circuit 96 also has outputs connected to lines 98 and 100 to provide control signals for setting the reference voltage levels.

While blocks 18, 34, 48, 56 and 74 are illustrated as being implemented by operational amplifiers with conventionally arranged discrete resistors and capacitors, it should be noted that the values of the passive components required may result in discrete components having physical sizes that are undesirably large in view of the generally recognized desirability of minimizing the overall size of implantable cardiac stimulators. It is therefore preferred that the illustrated functional blocks be implemented in an integrated circuit using known switched-capacitor technology.

Figure 2:
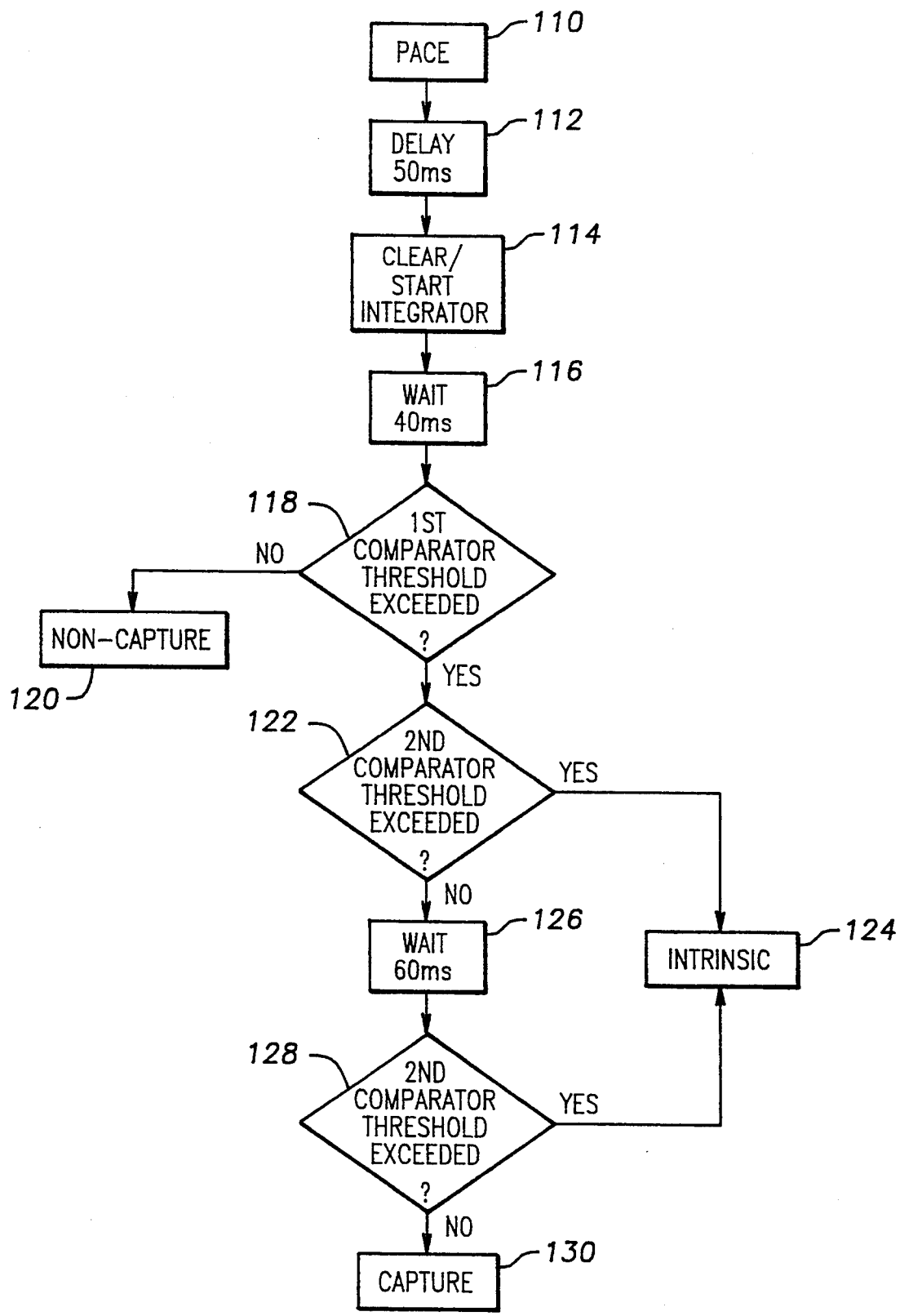
FIG. 2 is a flow chart of the operation of the control logic of FIG. 1.

Referring now to FIG. 2, there is illustrated a flow chart of the operation of control logic and microprocessor circuit 96, with reference to the circuit of FIG. 1, and with the assumption that the circuit of FIG. 1 has been implemented in an implantable cardiac stimulator of otherwise conventional arrangement. Starting at the top of the flow chart, the process of capture detection begins with delivery of a pacing pulse by the cardiac stimulator, indicated by box 110. Logic circuit 96 uses the pacing event as a marker from which subsequent timing is counted. Following the pacing event, there is a 50 msec delay, as indicated by box 112. At 50 milliseconds after the pacing event, a signal is generated on output line 84 to clear integrator 74 and begin a new integration period, as indicated by box 114. After having been cleared, integrator 74 continues integrating over an initial time window that is 40 msec in length, as indicated by box 116. At the end of the first time window, logic circuit 96 checks the output of first comparator 88 to determine whether the first comparator threshold (i.e. reference voltage 92) has been exceeded, as indicated by decision box 118. If the answer is no, then it is determined that capture has not occurred as indicated by box 120. If the answer is yes, it is tentatively determined that capture has occurred, but it is possible that the threshold of first comparator 88 has been exceeded due to the occurrence of an intrinsic contraction during the initial integration window rather than an evoked response indicative of capture. To identify intrinsic contractions, which tend to generate signals of much greater amplitude than evoked responses, control logic circuit 96 checks the output of second comparator 90 to determine whether the threshold of second comparator 90 (i.e. reference voltage 94) has been exceeded, as indicated by decision box 122. If the answer is yes, then it is determined that an intrinsic contraction has occurred, as indicated by box 124. If the answer is no, then the integrator 74 is permitted to continue integrating for an additional 60 msec, as indicated by box 126. At the end of the extended integration window, control logic circuit 96 checks the output of second comparator 90 again to determine whether the threshold of second comparator 90 (i.e. reference voltage 94) has been exceeded, as indicated by decision box 128. If the answer is no, meaning that the output of integrator 74 exceeded the threshold of the first comparator 88 within 90 msec after the stimulating pulse, but did not exceed the threshold of the second comparator 90 within 150 msec after the stimulating pulse, then it is determined that capture has occurred, as indicated by box 130. If the answer is yes, meaning that the output of integrator 74 exceeded the threshold of first comparator 88 within 90 msec after the stimulating pulse, and exceeded the threshold of second comparator 90 within 150 msec after the stimulating pulse, then it is determined that an intrinsic contraction has occurred, as indicated by box 124.

Figure 3:
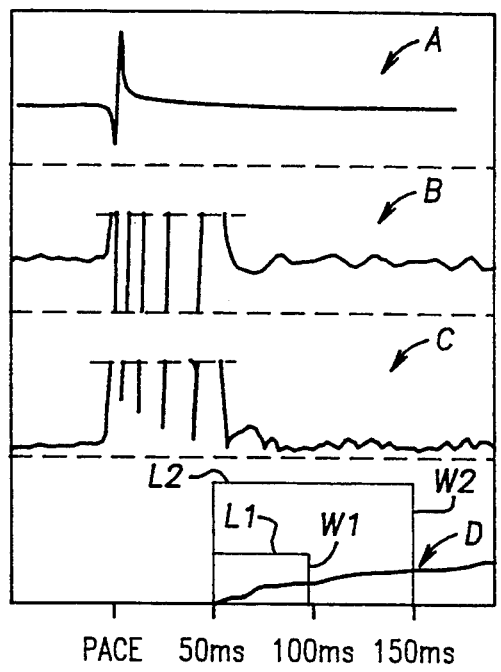
FIG. 3 is a graphic illustration of the signals at various stages of the circuit of FIG. 1, illustrating a representative non-capture event.

Referring to FIG. 3, there is illustrated a series of signal traces labeled A, B, C and D, involving a non-capture event. The top signal trace A represents the electrical potential that is present at the sensing electrode connected to input 14 of pre-amplifier 12 immediately following delivery of a stimulating pulse via that same electrode. At the scale shown, the evoked response, even if present, would not be visible because it would be dominated by the large-amplitude exponentially-decaying residual polarization charge. The next signal trace B represents the signal after having been amplified by pre-amplifier 12, filtered by filter stages 18 and 34, and amplified again by amplifier stage 48. The large amplitude excursions of the amplified and filtered signal in the first approximately 50 milliseconds following delivery of the pacing pulse are shown truncated so that the waveform thereafter can be more clearly seen. The next signal trace C represents the signal at the output of absolute value circuit 56. Again, the large amplitude excursions have been truncated for clarity. It should be recognized that the amplitude excursions of trace C in the period following the first approximately 50 milliseconds after delivery of the pacing pulse are relatively small. This is indicative of the absence of an evoked response signal, and of non-capture of the heart by the stimulating pulse. The last signal trace D represents the integrated signal at the output of integrator stage 74. As discussed above with respect to FIG. 2, integration takes place during a window of time that starts at approximately 50 milliseconds after delivery of the pacing pulse. An initial integration window W1 of approximately 40 milliseconds duration and having a first amplitude threshold level of L1 is superimposed on trace D. The threshold level L1 corresponds to the reference voltage 92 of first comparator 88. It can be seen that the integrated signal does not exceed the first threshold level L 1 during the 40 ms duration of window W1. This signal would therefore be classified as a non-capture.

Figure 4:
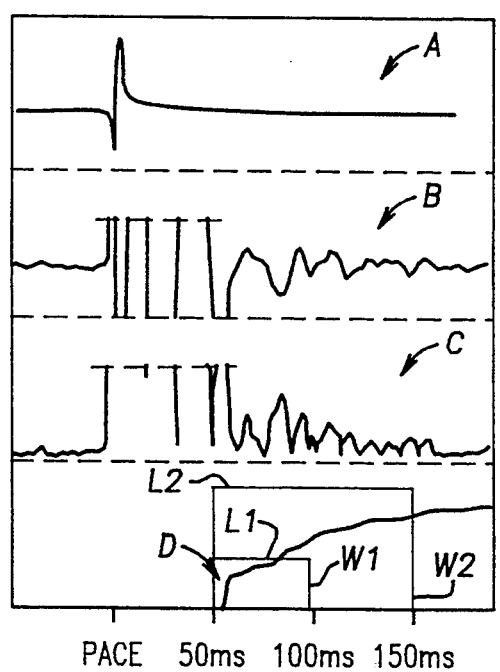
FIG. 4 is a graphic illustration of the signals at various stages of the circuit of FIG. 1, illustrating a representative capture event.

Referring now to FIG. 4, there is illustrated a series of signal traces labeled A, B, C and D involving a capture event. The top signal trace A represents the electrical potential that is present at the sensing electrode connected to input 14 of pre-amplifier 12 immediately following delivery of a stimulating pulse via that same electrode. At the scale shown, the evoked response, although present, is not visible due to the masking effect of the residual polarization charge on the stimulating/sensing electrode. The next signal trace B represents the electrical potential at sensing electrode 14 after having been amplified by pre-amplifier 12, filtered by filter stages 18 and 34, and amplified again by amplifier stage 48. As in FIG. 3, the large amplitude excursions of the amplified and filtered signal are shown truncated. The next signal trace C represents the signal at the output of absolute value circuit 56. Again, the large amplitude excursions have been truncated for clarity. It should be recognized that the amplitude excursions of trace C in the period following the first approximately 50 milliseconds after delivery of the pacing pulse are visibly greater than in the non-capture situation illustrated in FIG. 3. This is indicative of the presence of an evoked response signal characteristic of capture of the heart by the stimulating pulse. The last signal trace D represents the integrated signal at the output of integrator stage 74. As in FIG. 3, an initial integration window W1 of approximately 40 milliseconds duration and having a first amplitude threshold level of L1 is superimposed on trace D. It can be seen that the integrated signal exceeds the first threshold level L1 during the 40 ms duration of window W1. This signal would therefore be tentatively classified as a capture as of the end of the first integration window W1, provided that the integrated signal does not exceed a second threshold level L2 as of the end of the first integration window W1. The threshold level L2 corresponds to reference voltage 94 of second comparator 90. In FIG. 4, the signal does not exceed L2 within time window W1. Nevertheless, it is possible that an intrinsic depolarization occurred such that its signal is just beginning to contribute to the integrated signal during the initial window W1. Such an intrinsic event could be the cause of the integrated signal exceeding the first threshold. It is therefore desirable to continue integrating past the initial window W1 to distinguish a capture event from an intrinsic event. A second integration window W2 having a duration of about 150 ms is shown. In FIG. 4, the integrated signal has not exceeded the second threshold level L2 as of the end of the second integration window W2, thereby confirming that the signal is indeed indicative of a capture event and not an intrinsic depolarization.

Figure 5:
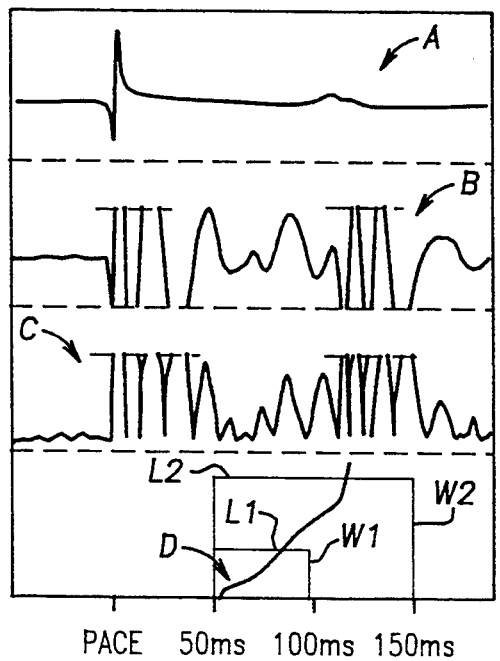
FIG. 5 is a graphic illustration of the signals at various stages of the circuit of FIG. 1, illustrating a representative intrinsic event.

Referring now to FIG. 5, there is illustrated a series of signal traces labeled A, B, C and D involving an intrinsic depolarization event. The top signal trace A represents the electrical potential that is present at the sensing electrode connected to input 14 of pre-amplifier 12 immediately following delivery of a stimulating pulse via that same electrode. An intrinsic depolarization is clearly visible at approximately 100 ms after delivery of the stimulating pulse. The next signal trace B represents the electrical potential at sensing electrode 14 after having been amplified by pre-amplifier 12, filtered by filter stages 18 and 34, and amplified again by amplifier stage 48. As in FIGS. 3 and 4, the large amplitude excursions of the amplified and filtered signal are shown truncated. The next signal trace C represents the signal at the output of absolute value circuit 56. Again, the large amplitude excursions have been truncated for clarity. It should be recognized that the amplitude excursions of trace C in the period following the first approximately 100 milliseconds after delivery of the pacing pulse are considerably greater than in the capture situation illustrated in FIG. 4. This is indicative of the presence of an intrinsic depolarization signal. The last signal trace D represents the integrated signal at the output of integrator stage 74. It can be seen that the integrated signal exceeds the first threshold level L1, but does not exceed threshold level L2, during the 40 ms duration of window W1. This signal would therefore be tentatively classified as a capture as of the end of the first integration window W1. Nevertheless, in this example an intrinsic depolarization occurred such that its signal is just beginning to contribute to the integrated signal during the initial window W1, and is the cause of the integrated signal exceeding the first threshold. To verify this, it is desirable to continue integrating past the initial window W1 to confirm the presence of an intrinsic event. In FIG. 5, the integrated signal has exceeded the second threshold level L2 as of the end of the second integration window W2, thereby confirming that the signal is indeed the result of an intrinsic depolarization.

It should be understood that in the illustrations of signal trace D in each 5 of FIGS. 3-5, the second threshold level L2 is not shown to scale for clarity. It is difficult to generalize the preferred levels for L1 and L2 since the signal levels involved will be highly dependent upon the overall gain characteristics of the particular implementation of the circuit of FIG. 1 in combination with the lead system used to sense heart activity. It has been found, however, that signal at the output of the integrator stage tends to be about an order of magnitude greater in the case of an intrinsic contraction as compared to a signal indicative of capture. Thus, for example, if the capture threshold L1 is set at 100 millivolts, L2 should be set at about 1 volt. Even for a given hardware system, there may be some patient to patient variation in optimal threshold level settings for L1 and L2. It is therefore desirable that control logic circuit 96 be configured to permit a range of adjustment of reference voltages 92 and 94, which implement the threshold levels L1 and L2.

It should also be understood that the integration time windows W1 and W2 as disclosed herein are the preferred windows for the disclosed filter characteristics and lead arrangement, but other time windows may be preferable with other implementations. There may also be some patient to patient variation that requires shifting the time windows for optimum results. It is therefore desirable that control logic circuit 96 be configured to permit a range of adjustment of the start time of the integration windows, and of the times at which the comparator outputs are checked. For example, it has been observed that with signal data collected from a bipolar lead system, as opposed to the disclosed unipolar system, better discrimination between capture and non-capture is obtained by shifting the windows W1 and W2 about 5 milliseconds earlier.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

I claim:

1. In a cardiac stimulator having an electrode and having a cardiac stimulation pulse generator means for delivering a cardiac stimulation pulse to the heart, the improvement comprising a capture detector for detecting an electrical signal at said electrode that is evoked in said heart in response to said cardiac stimulation pulse having:
   a highpass filter having an input in circuit communication with said electrode and having an output;
   an absolute value circuit having an input in circuit communication with the output of said highpass filter and having an output;
   an integrator having an input in circuit communication with the output of said absolute value circuit and having an output;
   a comparator having a first input in circuit communication with the output of said integrator and having a second input in circuit communication with a reference value, said comparator having an output; and
   means for causing said integrator to integrate over a selected window of time beginning at a selected time delay following delivery of said cardiac stimulation pulse;
   whereby said output of said comparator has a value that is indicative of whether capture has occurred.

2. The cardiac stimulator of claim 1, and further including a second comparator having a first input in circuit communication with the output of said integrator and having a second input in circuit communication with a second reference value, said second comparator having an output.

3. The cardiac stimulator of claim 2, in which the second reference value is greater than the first reference value.

4. The cardiac stimulator of claim 3, in which the second reference value is about an order of magnitude greater than the first reference value.

5. The cardiac stimulator of claim 2, in which said means for causing said integrator to integrate extends the window of integration in the event that the first comparator output indicates that the first input to the first comparator exceeded the reference value during the selected window of time.

6. The cardiac stimulator of claim 1, in which said highpass filter is adapted and configured to pass frequencies above about 40 Hz.

7. The cardiac stimulator of claim 1, and further including a bandpass filter having an input and an output and connected in circuit communication with said highpass filter in series connection therewith.

8. The cardiac stimulator of claim 7, in which said bandpass filter has a pass band of about 22 Hz to about 60 Hz.

9. The cardiac stimulator of claim 1, in which said means for causing said integrator to integrate extends the window of integration in the event that the comparator output indicates that the first input to the comparator exceeded the reference value during the selected window of time.

10. A method of verifying cardiac capture by sensing via a pacing electrode a cardiac signal evoked in response to a cardiac stimulation pulse delivered via said same pacing electrode, comprising the steps of:
    sensing a waveform signal at said pacing electrode following delivery of said cardiac stimulation pulse;
    bandpass filtering said sensed waveform signal through a pass band selected to pass a band of frequencies characteristic of the evoked cardiac signal;
    processing said bandpass-filtered waveform signal to render a waveform signal representing the absolute value of said bandpass-filtered signal;
    integrating said absolute value processed waveform signal over a selected window of time beginning at a selected time delay following delivery of said cardiac stimulation pulse; and
    comparing said integrated waveform signal to a reference value during said selected window of time and generating a capture detect signal if said integrated waveform signal exceeds said reference value during said selected window of time.

11. A method of verifying cardiac capture by sensing via an electrode a cardiac signal evoked in response to a cardiac stimulation pulse, comprising the steps of:
    sensing a waveform signal at said electrode following delivery of said cardiac stimulation pulse;
    highpass filtering said sensed waveform signal through a filter selected to pass frequencies characteristic of the evoked cardiac signal;
    processing said highpass-filtered waveform signal to render a waveform signal representing the absolute value of said bandpass-filtered signal;
    integrating said absolute value processed waveform signal over a selected window of time beginning at a selected time delay following delivery of said cardiac stimulation pulse; and
    comparing said integrated waveform signal to a reference value at the end of said selected window of time and generating a capture detect signal if said integrated waveform signal exceeds said reference value during said selected window of time.

12. The method of claim 11, in which the electrode via which the cardiac signal is sensed is the same electrode via which the stimulation pulse is delivered.

13. A method of verifying cardiac capture by sensing via an electrode a cardiac signal evoked in response to a cardiac stimulation pulse, comprising the steps of:
sensing a waveform signal at said electrode following delivery of said cardiac stimulation pulse;
bandpass filtering said sensed waveform signal through a pass band selected to pass a band of frequencies characteristic of the evoked cardiac signal;
processing said bandpass-filtered waveform signal to render a waveform signal representing the absolute value of said bandpass-filtered signal;
integrating said absolute value processed waveform signal over a selected window of time beginning at a selected time delay following delivery of said cardiac stimulation pulse; and
comparing said integrated waveform signal to a first reference value at the end of said selected window of time, and comparing said integrated waveform signal to a second reference value at the end of said selected window of time, and generating a capture detect signal if said integrated waveform signal exceeds said first reference value during said selected window of time, but does not exceed said second reference value during said selected window of time.

14. The method of claim 13, in which said second reference value is greater than said first reference value.

15. A method of verifying cardiac capture by sensing via an electrode a cardiac signal evoked in response to a cardiac stimulation pulse, comprising the steps of:
sensing a waveform signal at said electrode following delivery of said cardiac stimulation pulse;
bandpass filtering said sensed waveform signal through a pass band selected to pass a band of frequencies characteristic of the evoked cardiac signal;
processing said bandpass-filtered waveform signal to render a waveform signal representing the absolute value of said bandpass-filtered signal;
integrating said absolute value processed waveform signal over a selected window of time beginning at a selected time delay following delivery of said cardiac stimulation pulse; and
comparing said integrated waveform signal to a first reference value at the end of said selected window of time, and comparing said integrated waveform signal to a second reference value at the end of said selected window of time, and if said integrated waveform signal exceeds said first reference value during said selected window of time, but does not exceed said second reference value during said selected window of time, continuing to integrate said absolute value processed waveform signal over an extended window of time, and generating a capture detect signal if said integrated waveform signal does not exceed said second reference value during said extended window of time.

* * * * *